United States Patent [19]
Cubicciotti

[11] Patent Number: 5,695,990
[45] Date of Patent: Dec. 9, 1997

[54] PHYCOBILISOMES, DERIVATIVES, AND USES THEREFOR

[76] Inventor: Roger S. Cubicciotti, 258 Midland Ave., Montclair, N.J. 07042

[21] Appl. No.: 420,726

[22] Filed: Apr. 10, 1995

[51] Int. Cl.$^6$ .................................................. C12N 1/00
[52] U.S. Cl. ........................... 435/317.1; 435/4; 435/7.1; 435/7.2; 435/7.8; 435/963; 530/402; 530/391.3; 436/518; 436/519; 436/524; 436/527; 436/536
[58] Field of Search .............................. 435/317.1, 4, 7.1, 435/7.2, 7.8, 963; 436/536, 518, 519, 524, 527; 530/402, 391.3

[56] References Cited

U.S. PATENT DOCUMENTS

| | | | |
|---|---|---|---|
| 3,934,369 | 1/1976 | Rebeiz | 435/118 |
| 4,320,050 | 3/1982 | Rebeller et al. | 530/414 |
| 4,520,110 | 5/1985 | Stryer et al. | 436/501 |
| 4,542,104 | 9/1985 | Stryer et al. | 436/536 |
| 4,666,862 | 5/1987 | Chan | 436/501 |
| 4,745,285 | 5/1988 | Recktenwald et al. | 250/458.1 |
| 4,857,474 | 8/1989 | Waterbury et al. | 436/501 |
| 4,859,582 | 8/1989 | Stryer et al. | 435/5 |
| 5,055,556 | 10/1991 | Stryer et al. | 530/370 |
| 5,171,846 | 12/1992 | Gupta | 530/400 |
| 5,272,257 | 12/1993 | Gupta | 530/370 |
| 5,281,698 | 1/1994 | Nitecki | 530/351 |

OTHER PUBLICATIONS

Papageorgiou et al., "Effects of Chaotropic Electrolytes on the Structure and Electronic Excitation Coupling of Glutaraldehyde– and Diimido Ester–cross linked Phycobilisomes", *Biochimica et Biophysica Acta* 724:323–332 (1983).
Gekko et al., "Mechanism of Protein Stabilization by Glycerol–Water Mixtures", *Biochemistry* 20:4667–4676 (1981).
Wang et al., "Parenteral Formulations of Proteins and Peptides: Stability and Stabilizers", *J. Parenteral Science and Technology* 42(2S):S3–S26 (1988).
Colagan et al., *Current Protocols in Immunology*, New York; Greene Associates and Wiley Interscience, 1991, pp. 2.0.1–2.0.4, 2.1.1–2.1.22, 2.2.1–2.2.6, 2.3.1–2.3.4.
Gantt et al., "Phycobilisomes: A Terminal Acceptor Pigment in Cyanobacteria and Red Algae", *Molecular Biology of the Photosynthetic Apparatus*, 1985 Cold Spring Harbor laboratory pp. 223–229.
Gantt, "Phycobilisomes", *Photosynthesis III: Photosynthetic Membranes and Light Harvesting Systems* (L.A. Strachelin and C.J. Arntzen, eds.), pp. 260–268, Spring–Verlag, NY (1986).
Grossman et al., "The Phycobilisome, a Light–Harvesting Complex Responsive to Environmental Conditions", *Microbiological Reviews* 57(3):725–749 (1993).
Rigbi et al., "Cyanobacterial Phycobilisomes: Selective Dissociation Monitored by Fluorescence and Circular Dichroism", *Proc. Natl. Acad. Sci. USA* 77(4):1961–1965 (1980).
Biggins, "Mechanism of the Light State Transition in Photosynthesis", *Biochimica et Biophysica Acta* 724:111–117 (1983).

Glazer et al., "Phycofluor Probes", *TIBS*, Oct. 1994, pp. 423–427.
Glazer, "Phycobilisomes: Structure and Dynamics of Energy Flow", *Molecular Biology of the Photosynthetic Apparatus*, 1985 Cold Spring Harbor Laboratory, pp. 231–239.
Apt et al., "Characterization and Transcript Analysis of the Major Phycobiliprotein Subunit Genes from *Aglaothamnion neglectum* (Rhodophyta)", *Plant Molecular Biology* 21:27–38 (1993).
Apt et al., "Genes Encoding Phycobilisome Linker Polypeptides on the Plastid Genome of *Aglaothamnion neglectum* (Rhodophyta)", *Phtosynthesis Research* 35:235–245 (1993).
Cohen–Bazire et al., "Chapter 7: Phycobilisomes: Composition and Structure", *The Biology of Cyanobacteria*, Carr NG and Whitton BA (eds), Univ. of Cal Press, Berkeley & LA, pp. 143–190 (1982).
Bennett et al., "Properties of Subunits and Aggregates of Blue–Green Algal Biliproteins", *Biochemistry* 10(19):3625–3634 (1971).
Brimble et al., "Pigment Orientation and Excitation Energy Transfer in *Porphyridium cruentum* and *Synechococcusi* sp. PCC 6301 Cross–Linked in Light State 1 and Light State 2 with Glutaraldehyde", *Biochem. & Biophys. Acta*, 973:315–323 (1989).
Bruce et al., "State Transitions in a Phycobilisome–Less Mutant of th eCyanobacterium *Synechococcus* sp. PCC 7002", *Biochimica et Biophysica Acta* 974:66–73 (1989).
Bruns et al., "Molecular Characterization of Phycobilisome Regulatory Mutants of *Fremyella diplosiphon*", *J. Bacteriology* 171(2):901–908 (1989).
Bryant et al., "Characterization of the Biliprotiens of *Gloeobacter violaceus*", *Arch. Microbiology* 129:190–198 (1981).
Bryant, "Phycobilisomes of *Synechococus* Sp. PCC 7002, *Pseudanabaena* SP. PCC 7409, and *Cyanophora paradoxa*: an Analysis by Molecular Genetics", *Photosynthetic Light–Harvesting Systems*, Scheer H, Schneider S. (eds), Walter de Gruyter & Co., NYC (1988).
Canaani et al., "Formation of Hybrid Phycobilisomes by Association of phycibiliproteins from nostoc and Fremyella", *Proc. Natl. Acad. Sci. USA* 79:5277–5281 (1982).
Canaani et al., "Reassembly of Phycobilisomes from Allophycocyanin and a Phycocyanin–Phycoerythrin Complex", *FEBS Letters* 115(2):225–229 (1980).
Collier et al., "A Small Polypeptide Triggers Complete Degradation of Light–Harvesting Phycobiliprotiens in Nutrient–Deprived Cyanobacteria", *The EMBO Journal* 13(5):1039–1047 (1994).

(List continued on next page.)

*Primary Examiner*—Paula K. Hutzell
*Assistant Examiner*—Heather A. Bakalyar
*Attorney, Agent, or Firm*—Banner & Witcoff, Ltd.

[57] ABSTRACT

Methods and compositions are provided for use of modified or intact phycobilisomes as extremely potent labels in sensitive monitoring kits (e.g., for blood contamination), specific binding assays (e.g., visual, photometric and fluorometric immunoassays) and optoelectronic devices (e.g., biosensors, photoelectric transducers).

32 Claims, No Drawings

OTHER PUBLICATIONS

Conley et al., "Genes Encoding Major Light-Harvesting Polypeptides are Clustered on the Genome of the Cyanobacterium *Fremyella diplosiphon*", *Proc. Natl. Acad. Sci, USA* 83:3924-3928 (1986).

Gagliano et al., "Orientation of Pigments in Phycobilisomes of *Porphyridium* sp. Lewin. A Linear Dichroism Study Utilizing Electric and Gel Orientation Methods", *Biochim. & Biophys. Acta* 808:455-463 (1985).

Gantt, "Phycobilisomes: Assessment of the Core Structure and Thylakoid Interaction", *Light-Energy Transduction in Photosynthesis: Higher Plant and Bacterial Models*, Stevens SE, Bryant DA (eds), American Society of Plant Physiologists, pp. 91-101 (1988).

Gantt et al., "Photosystem II-Phycobilisome Complex Preparations", *Methods in Enzymology* 267:286-290 (1988).

Gantt et al., "Phycobiliprotein Localization in Algae", *Energy Conversion by the Photosynthetic Apparatus*, No. 19:393-405 (1967).

Gantt, "Properties and Ultrastructure of Phycoerythrin from *Porphyridium cruentum*", *Plant Physiol.* 44:1629-1638 (1969).

Gantt, "Phycobilisomes from Blue-Green and Red Algae", *Plant Physiol.* 63:615-620 (1979).

Gantt et al., "Phycobilisomes of *Porphyridium cruentum*", *J. Cell Biol.* 54:313-324 (1972).

Gantt et al., "Granules Associated with the Chloroplast Lamellae of *Porphyridium cruentum*," *J. Cell Biol.* 29:423-434 (1966).

Gantt et al., "The Ultrastructure of *Porphyridium cruentum*", *J. Cell Biol.* 26:365-381 (1965).

Gingrich et al., "Core Substructure in Cyanobacterial Phycobilisomes", *J. Cellular Biochemistry* 22:1-14 (1983).

Glazer et al., "Kinetics of Energy Flow in the Phycobilisome Core", *Science* 230:1051-1053 (1985).

Glazer, "Light Harvesting by Phycobilisomes", *Ann. Rev. Biophys. Chem.* 14:47-77 (1985).

Glazer, "Light Guides", *J. Biological Chemistry* 264(1):1-4 (1989).

Glazer, "Phycobilisome: A Macromolecular Complex Optimized for Light Energy Transfer", *Biochimica et Biophysica Acta* 768:29-51 (1984).

Glazer, "Structure and Molecular Organization of the Photosynthetic Accessory Pigments of Cyanobacteria and Red Algae", *Mol. Cell Biochem.* 18:125-139 (1977).

Glazer et al., "Fluorescent Tandem Phycobiliprotein Conjugates", *Biophys. J. Biophysical Society* 43:383-386 (1983).

Glazer et al., "Formation of Hybrid Proteins from the α and β Subunits of Phycocyanins of Unicellular and Filamentous Blue-Green Algae", *J. Biol. Chem.* 248:663-671 (1973).

Glick et al., "Role of Colorless Polypeptides in Phycobilisome Reconstitution from Separated Phycobiliproteins", *Plant Physiol.* 69:991-997 (1982).

Grossman et al., "A Rapid Procedure for the Isolation of Intact Phycobilisomes", *Carnegie Inst. Wash. Yearbook* 82:116120 (1983).

Guglielmi et al., "The Structure of *Gloeobacter violaceus* and its Phycobilisomes", *Arch. Microbiology* 129:181-189 (1981).

Houmard et al., "Genes Encoding Cor Components of the Phycobilisome in the Cyanobacgerium *Calothrix* sp. Strain PCC 7601: Occurrence of a Multigene Family", *J. Bacteriology* 170(12):5512-5521 (1988).

Katoh et al., "Photosynthetic Vesicles with Bound Phycobilisomes from *Anabaena variabilis*", *Biochimica et Biophysica Acta* 546:383-393 (1979).

Katoh, "Phycobilisome Stability", *Methods in Enzymology* 167:313-318 (1988).

Kirilovsky et al., "Functional Assembly in Vitro of Phycobilisomes with Isolated Photosystem II Particles of Eukaryotic Chloroplasts", *J. Biol. Chem.* 261(26):12317-12323 (1986).

Kronick et al., "Immunoassay Techniques with Fluorescent Phycobiliprotein Conjugates", *Clin. Chem.* 29/9:1582-1586 (1983).

Lipschultz et al., "Association of Phycoerythrin and Phycocyanin: In Vitro Formation of a Functional Energy Transferring Phycobilisome Complex of *Porphyridium sordidum*", *Biochemistry* 20:3371-3376 (1981).

Clement-Metral et al., "Fluorescence Transfer in Glutaraldehyde Fixed Particles of the Red Alga *Porphyridium cruentum* (N)", *FEBS Letters* 12(4):225-228 (1971).

Clement-Metral et al., "Isolation of Oxygen-Evolving Phycobilisome-Photosytem II Particles from *Porphyridium cruentum*", *FEBS Letters* 156(1):185-188 (1983).

Rosinski et al., "Phycobilisome Ultrastructure and Chromatic Adaptation in *Fremyella diplosiphon*," *Ann. Bot.* 47:1-12 (1981).

Shen et al., "*Synechocystis* sp PCC 6803 Strains Lacking Photosystem I and Phycobilisome Function", *The Plant Cell* 5:1853-1863 (1993).

Sofrova et al., "Crosslinking of Isolated Phycobilisomes with Dimethyl Suberimidate", *Photosynthesis III. Structure and Molecular Organisation of the Photosynthetic Aparatus*, edited by George Akoyunoglou, Balaban International Science Services, Philadelphia, PA (1981).

Yamanaka et al., "Molecular Architecture of a Light-Harvesting Antenna", *J. Biological Chemistry* 257(8):4077-4086 (1982).

Wolfe et al., "Evidence for a Common Origin of Chloroplasts with Light-Harvesting Complexes of Different Pigmentation", *Nature* 367:566-568 (1994).

PHYCOBILISOMES, DERIVATIVES, AND USES THEREFOR

BACKGROUND OF THE INVENTION

Phycobilisomes are complexes of phycobiliproteins and colorless polypeptides which function as the major light harvesting antennae in blue-green and red algae. Gantt, (1975) "Phycobilisomes: light harvesting pigment complexes," *BioScience* 25: 781-788. The major criterion for the functional integrity of these complexes is the demonstration that they exhibit highly efficient transfer of energy between component phycobiliproteins, for example, in *Porphyridium cruentum* phycobilisomes from phycoerythrin (PE) to phycocyanin (PC) and finally to allophycocyanin (APC). The colorless polypeptides are involved in the assembly and positioning of the phycobiliproteins within the phycobilisomes for proper stability and energy transfer.

Phycobilisomes from different organisms share a number of common properties, including: (1) extremely high "complex molecular weights" ($5-20 \times 10^6$ daltons) i.e., the weight of one mole of a phycobilisome complex comprised of multiple molecules; (2) multiple absorption maxima in the visible range of the electromagnetic spectrum; (3) high molar absorptivities ($e_{max} > 10^7 M^{-1}$ cm$^{-1}$); (4) efficient (>90%) directional vibrational energy transfer among constituent phycobiliproteins, commonly from one or more sensitizing species to a terminal acceptor capable of fluorescence; (5) large Stoke's shifts relative to isolated phycobiliproteins; (6) high quantum yields of constituent phycobiliproteins; (7) high solubility in aqueous buffers; and (8) allophycocyanin-containing core structures.

Isolated phycobilisomes readily dissociate into free phycobiliproteins and a variety of phycobiliprotein complexes under all but the most favorable conditions. Low to moderate ionic strength (<0.5M phosphate), low phycobilisome concentration (<1 mg/ml), and low temperatures lead to dissociation of phycobilisomes. Katoh, (1988) *Methods in Enzymology* 162:313-318; Gantt et al., (1979) *Plant Physiology* 63:615-620. Freezing of algae is also reported to lead to destruction of phycobilisomes. Gantt et al., (1972) *Journal of Cell Biology* 54:313-324.

Morphologically, phycobilisomes are complex assemblies of oligomeric phycobiliprotein discs arranged in ordered stacks referred to as "rods". In general, several arm-like rods radiate out from a core assembly, also comprised of rods. Phycobilisomes from different organisms are morphologically and stoichiometrically diverse, having different numbers and types of constituent phycobiliproteins and rods. In general, peripheral rods are comprised of phycoerythrocyanin, phycoerythrin, and/or phycocyanin, and the core is comprised of allophycocyanin and associated linker proteins.

Isolated phycobiliproteins, the component fluorescent proteins of phycobilisomes, have been used as labels in immunoassays. See e.g., Stryer et al., U.S. Pat No. 4,520,110 and Kronick et al. (1983) *Clinical Chemistry* 29:1582-1586. However, because of the difficulty in isolating and manipulating intact phycobilisomes, the art has not recognized that these macromolecular assemblies could be similarly utilized. Because the signal which phycobilisomes can provide is theoretically so much larger than isolated phycobiliproteins, there is a need in the art for methods of treating phycobilisomes so that they can be used as detectable markers for a host of assays and other applications.

SUMMARY OF THE INVENTION

It is an object of the invention to provide a preparation of soluble phycobilisomes useful as labels for specific binding assays.

It is another object of the invention to provide a preparation of phycobilisome conjugates comprising phycobilisomes which are covalently attached to ligands, receptors, or other useful molecules.

It is another object of the invention to provide a preparation of immobilized phycobilisomes suitable for use in specific binding assays.

It is still another object of the invention to provide a method of performing assays using phycobilisomes as detectable labels.

These and other objects of the invention are provided by one or more of the embodiments described below. In one embodiment of the invention, a homogeneous preparation of isolated, soluble, stabilized phycobilisomes is provided. The phycobilisomes do not settle at 1×g within 24 hours. Moreover, upon centrifugation at 1,000×g for 5 minutes, greater than 55% of the phycobilisomes remain in the supernatant.

According to another embodiment of the invention a preparation of phycobilisomes which are covalently attached to a molecular species is provided. The molecular species is selected from the group consisting of ligands, receptors, and signal-generating molecules.

In another embodiment of the invention a preparation of isolated phycobilisomes is provided in which the phycobilisomes are noncovalently bound to a polyspecific, polyvalent ligand or receptor.

According to yet another embodiment of the invention a preparation of isolated, functionally intact phycobilisomes is provided in which the phycobilisomes are immobilized on a solid support.

According to still another embodiment of the invention a method for performing a specific binding assay is provided. According to the method, an analyte is measured by means of its ability to specifically bind to a specific binding partner, and an assay component is detectably labeled. The assay component is selected from the group consisting of: the specific binding partner, reagent molecules having the same chemical identity as the analyte, and reagent molecules having the same binding specificity as the analyte. The improvement provided by the present invention is the use of a signal-generating system comprising phycobilisomes as the detectable label. The phycobilisomes may be attached to the specific binding partner, to the reagent molecules having the same chemical identity as the analyte, to the reagent molecules having the same binding specificity as the analyte, or to a ligand or receptor which specifically binds to the assay component. The attachment may be by a covalent bond or by noncovalent means. The phycobilisomes may be stabilized. The assay may be a homogeneous assay in which binding of the analyte to the specific binding partner is measured without separation of bound form unbound specific binding partner. The signal-generating system employed in the assay may further comprise a terminal acceptor molecule capable of fluorescence upon transfer of directional energy from said phycobilisomes. The phycobilisomes may be prepared for use by freezing or dehydration.

According to still another embodiment of the invention a method for performing a specific binding assay is provided in which an analyte is measured by means of its ability to specifically bind to a specific binding partner (ligand or receptor). As provided herein, phycobilisomes are used to label either an analog of the analyte or a specific binding partner of the analyte.

These and other embodiments of the invention provide the art with an extremely sensitive, nonisotopic detection means for assaying analytes. Unlike enzymatic labels, phycobilisomes can be quantitatively detected without accessory substrates, chromogens, cofactors, or timed incubations.

DETAILED DESCRIPTION OF THE PREFERRED EMBODIMENTS

It is a discovery of the present invention that phycobilisomes can be stabilized, conjugated, or modified so that they can be used intact in a variety of assays and formats. Phycobilisomes provide labels of high sensitivity due inter alia to their extremely large molecular weights, extinction coefficients, and energy transfer efficiencies, as well as to the high quantum yields of constituent phycobiliproteins. Directional energy transfer within phycobilisomes occurs from one or more "sensitizing species" to a terminal acceptor. A sensitizing species is a first fluorophor having an emission peak capable of exciting a second ("acceptor" or "emitter") fluorophor. Such energy transfer has application in homogeneous specific binding assays and in transducers comprising immobilized phycobilisomes.

Methods of producing homogeneous preparations of isolated, soluble, stabilized phycobilisomes are provided. The homogeneity of phycobilisome preprations can be demonstrated by lack of settling within a 24-hour incubation at 1×g. Solubility can be assessed by centrifugation. "Soluble phycobilisome preparation" means that upon centrifugation at 1,000×g for 5 minutes, greater than 55% of the phycobilisomes remain in the supernatant. It is desirable that greater than 65%, 75%, 85%, and even 90% of the phycobilisomes remain in the supernatant after such centrifugation, and such levels are possible using the methods of the present invention. Typically, the phycobilisomes are stabilized by means of a gentle crosslinking treatment, such as with formaldehyde or very low concentrations of glutaraldehyde. Other medium-, short- or zero-length crosslinking reagents may also be used. Stabilized phycobilisomes are stable even under conditions of dilute ionic strength (<0.5M) and protein concentration (<1 mg/ml), in contrast with native phycobilisomes. In addition, they are stable in the presence of glycerol, sucrose, and polyethylene glycol. Phycobilisomes which are functionally intact have a major emission peak at the wavelength of the terminal acceptor.

Specific chemical groups can be added to phycobilisomes by quenching the stabilization reactions with suitable substances, including but not limited to cysteine, lysine, glutamic acid, glucosamine, etc. Such chemical groups can be useful for the further coupling of distinct molecular species, such as receptors, ligands, or signal-generating molecules to phycobilisomes. Added functional groups can also be used to dimerize or polymerize the phycobilisomes for use as stabilized, isolatable complexes.

Attached molecular species may be, but need not be, conjugated to phycobilisomes through added chemical groups. Alternatively, they can be directly attached during the stabilization reaction, such as with formaldehyde or glutaraldehyde. They can also be attached via different spacer arms to alter the spatial or stereochemical relationship between the molecular species and the phycobilisome. Ligands include but are not limited to agonists, antagonists, haptens, antigens, drugs, hormones transmitters, cofactors, vitamins, toxins, oligonucleotides, and conjugates formed by attaching any of these molecules to a second molecule. Receptors include but are not limited to antibodies, antibody fragments, antibody mimetics, molecular recognition units, adhesion molecules, soluble receptors, nucleic acids, membrane receptors, cellular receptors, and drug receptors. Signal-generating molecules include, but are not limited to, phycobiliproteins, dye molecules, colloids, fluorophores, enzymes, luminescent compounds, oxidizing and reducing compounds, and even other phycobilisomes.

Attachment of a molecular species to a phycobilisome may be site-specific, i.e., to a particular portion of a phycobilisome, to orient the light collection properties of this invention. This may be achieved inter alia by means of polyvalent receptors, such as antibodies, which are specific for one of the component proteins of the phycobilisome. A polyvalent receptor contains two or more binding sites for its ligand. The polyvalent receptors utilized in the present invention may be polyspecific, i.e., they may contain binding sites for two or more distinct ligands. Thus the polyspecific receptors can be used to link a phycobilisome to another species of molecule. Phycobilisomes can also be covalently attached to receptors or ligands by numerous methods well-known in the art of protein conjugation (cf. Tijssen[1], Wong[2] and Pierce[3] and references therein, included herein by reference).

[1]Tijssen, P. (1985). *Practice and Theory of Enzyme Immunoassays*. R. H. Burdon and P. H. van Knippenberg (Eds.) Laboratory Techniques in Biochemistry and Molecular Biology, Volume 15, Elsevier, New York.
[2]Wong, S. S. (1991). *Chemistry of Protein Conjugation and Crosslinking*, CRC Press, Boca Raton.
[3]Pierce Catalog & Handbook (1994) Cross-linking/Protein Modification, pp. 155–200.

Phycobilisomes may also be immobilized to a manufactured solid support, such as a microtiter dish, microparticle, polymeric bead, polymer matrix, synthetic membrane, liposome, etc. Such immobilization does not include the attachment of phycobilisomes to the thylakoid membrane as occurs physiologically, via specific receptors in the thylakoid membrane. The phycobilisomes are first isolated from algal cells and then attached to the solid support, or they may be modified, conjugated, or stabilized, prior to attachment. The attachment may be covalent or noncovalent, specific or non-specific. The method of attachment may be optimized to achieve a preferred orientation of the phycobilisomes relative to the solid surface. A single type of constituent phycobilisome protein, either linker protein or phycobiliprotein, may be used as the attaching moiety to the solid support. For some applications it may be desirable that the phycobilisomes be attached in an ordered array, such as in a grid or other pattern.

The phycobilisomes of the present invention are particularly well-suited for use in specific binding assays. These may be immunological assays, immunohistochemistry, cytometry, cell sorting, ligand- or receptor-binding assays, protein-protein binding assays, protein-nucleic acid binding assays, and even nucleic acid-nucleic acid binding (hybridization) assays. The phycobilisomes are typically used to label one of the specific binding partners involved in the assay. For example, the phycobilisomes may be used to label a ligand or receptor that specifically binds to the analyte to be assayed. Alternatively, the phycobilisomes may be used to label a reagent molecule which is a ligand or receptor that competes with the analyte for specific binding to its specific binding partner. Labeling may be direct, wherein the phycobilisomes are attached to a first ligand or receptor that specifically binds to, or competes with the analyte. Alternatively, labeling may be indirect, wherein the phycobilisomes are attached to a second ligand or receptor that specifically binds to a first ligand or receptor. The attachment of phycobilisomes to a specific binding partner may be covalent or non-covalent. The phycobilisomes may also be part of a signal-generating system in which other fluorophores emit light upon transfer of directional energy from phycobilisomes. The phycobilisome may be stabilized prior to its attachment to the specific binding partner or may be directly conjugated thereto. Alternative means of preparation of phycobilisomes include freezing, freeze-drying, and other methods of dehydration. It is desirable that freezing of phycobilisomes be done in the presence of sucrose, in concentrations from 0.1 to 1M. Other stabilizing agents such as sugars, salts, polymers, and cosolvents may be used. Particularly useful agents include trehalose, sorbitol, and dextran.

For use in specific binding assays, phycobilisomes can be conjugated to ligands, receptors, and/or signal-generating molecules by one-step, two-step, or multi-step methods. One-step glutaraldehyde methods proved effective and convenient for sequential stabilization and conjugation of phycobilisomes without intervening purification steps.

Any assay format known in the art may be utilized, including without limitation, homogeneous assays, heterogeneous assays, competitive assays, and sandwich assays. In homogeneous assays binding of the two binding partners (e.g., ligand and receptor) influences activity of the label; no separation of bound and unbound reagents is required. In heterogeneous assays separation of bound and free reagents is required to determine the amount of binding which has occurred. Quantification of such assays can be accomplished by either photometric, fluorometric or optoelectronic means. Alternatively, qualitative results can be obtained by visual inspection. Because native phycobilisomes spontaneously dissociate under routine conjugation and assay conditions, they must be stabilized prior to use in most conventional assay formats.

In heterogeneous specific binding assays, a reaction mixture is formed by contacting a liquid medium with a labeled conjugate comprising a phycobilisome attached to a specific binding partner. A bound phase and a free phase of said labeled conjugate are formed. The relative proportion of labeled conjugate in the two phases is a function of the presence and amount of ligand in the liquid medium. The bound phase and free phase are then separated. The ligand in the liquid medium is determined by detecting or measuring phycobilisomes in the bound phase or in the free phase.

A homogeneous specific binding assay method can also be readily performed. In a preferred method, a phycobilisome-labeled ligand or receptor is used in conjunction with a second fluorphore-labeled specific binding partner. Directional energy transfer within phycobilisomes enables their use as efficient photon donors or acceptors in such fluorescence energy transfer assays.

Phycobilisome-based assays can be detected electrochemically as well as fluorometrically, suggesting utility of "phycobilisome electrodes" as alternatives to enzyme electrodes commonly used in amperometric immunosensors. In addition, directional and intimate coupling of phycobilisomes to well-established microelectronic devices (e.g., photodiodes, charge-coupled devices) may provide means for efficient photoelectronic signal transduction on a submicron scale. Contemplated herein are microminiaturized "biotransducers" such as photoelectric converters, transistors, switches and amplifiers responsive to directional light energy transfer from immobilized, structurally oriented phycobilisomes.

Soluble, stabilized phycobilisomes of the present invention have a number of uses that do not require conjugation to specific binding partners. For example, they can be used as sensitive tracers for dilution and perfusion studies and as molecular size markers for analytical techniques. In a preferred embodiment, they can be used to detect potentially hazardous spills. Phycobilisomes can be mixed with a potentially hazardous substance prior to its use to yield a final concentration of phycobilisomes of less than about ten parts per million. The phycobilisomes can then be detected in the event that the hazardous substance is accidentally spilled or removed from its proper location. The presence of the detectable phycobilisomes indicates that a spill has occurred.

Phycobilisomes, according to the present invention, are self-assembling complexes of phycobiliproteins and linker proteins comprising at least one rod. The phycobilisomes of the present invention may be obtained from either prokaryotic cyanobacteria (blue-green algae) or eukaryotic red algae. The algae may be wild-type, mutants, hybrids, or genetic recombinants capable of expressing phycobilisome constituents. The algae may be harvested from natural environments (the wild) or grown under artificially controlled conditions. Such artificial conditions may simulate a natural environment or they may be designed to induce chromatic adaption, for example, to modulate the composition of phycobilisomes. Artificial conditions may require either autotrophic, mixotrophic, or heterotrophic growth.

Phycobilisomes may be isolated from the producing organisms after being stabilized in situ prior to cell disruption or in membrane-bound form following cell disruption. Alternatively, phycobilisomes may be isolated intact prior to in vitro stabilization or conjugation or immobilization. In yet another mode of operation, phycobiliproteins and linker proteins can be isolated and reconstituted in vitro to form phycobilisomes.

Stabilization methods which are embraced by the present invention include covalent as well as non-covalent means. Covalent methods include crosslinking and multi-point attachment of polymers that span at least two phycobilisome constituent proteins. Crosslinking agents may be zero-length (involving the direct attachment of two phycobilisome groups without intervening spacer atoms) or they may include spacer arms of varying length. Non-covalent stabilization may be accomplished using cosolvents, such as salts and sugars, affinity-based interactions, such as with certain polymers or polyvalent receptors, or changes in physical state, such as freezing or dehydrating.

For achieving conjugation of phycobilisomes to other molecular species, any conjugation method known in the art may be used. Direct attachment may be used or secondary structures such as spacer arms or carrier molecules may be interposed.

Immobilization of phycobilisomes to a solid support may be by means of a covalent or non-covalent linkage. Non-covalent methods include passive adsorption, affinity-based methods, encapsulation, entrapment and controlled deposition. Immobilization may yield a structurally ordered product. The phycobilisomes may be oriented in a particular manner with respect to the solid support (e.g., "core up" or "core down"). Alternatively the spacing between phycobilisomes on the solid support may be defined or patterned, for example, to form a two-dimensional array or grid.

Specific binding assays according to the present invention may be qualitative or quantitative. Small molecules (involving a single binding site) or large molecules (involving more than one binding site) may be used as analytes. Detection means for determining the results of the binding assay may be by visual inspection, photometry, fluorometry, or electrochemical means.

PHYCOBILISOME ISOLATION

General procedures for isolation of phycobilisomes from a wide range of unicellular algae have been described (e.g., Gantt et al. (1979) Plant Physiol. 63: 615–620). Phycobilisomes can be isolated from red algae (e.g., *Porphyridium cruentum*) and blue-green algae (e.g., *Anabaena variabilis, Spirulina platensis*,) by methods modified from those of Gantt and Lipschultz (1972) J. Cell Biol. 54:313–324. Up to 24 grams wet weight of biomass can be conveniently handled using six 35 ml centrifuge tubes in an SW27 rotor for the final sucrose gradient ultracentrifugation step. Phycobilisome recovery is on the order of 0.1–1.0% of initial biomass.

ISOLATION OF PHYCOBILISOMES FROM RED AND BLUE-GREEN ALGAE BY GRADIENT ULTRACENTRIFUGATION

Freshly cultured or frozen (–20° C. or –70° C.) algae can be cultured autographically in 40–500 L stirred tanks with continuous fluorescent illumination and harvested by centrifugation. *Porphyridium cruentum* (*P. cruentum*) can be grown at 20°–22° C. in an artificial seawater medium (pH 8.0) comprising sodium salts, Tadros Metals, Instant Ocean and Dunaliella vitamins. *Anabaena variabilis* can be grown at 25° C. in double-strength BG-11 medium containing sodium and potassium salts, magnesium sulfate, calcium chloride, citric acid, ferric ammonium citrate and A5 Metals (pH 7.8).

Unless otherwise specified, all preparative steps can be performed at room temperature (20°–23° C.) in 0.75M potassium phosphate (pH 7.0–7.2) containing 0.05% sodium azide (KPi buffer). Twenty four grams (wet weight) of packed cells are resuspended in 48 ml KPi buffer. PMSF (1 mM), benzamidine (5 mM) and DNase I (10 ul of RNase-free stock at 10 U/ul) are then added, and the suspension is passed four times in 15 ml increments through a French pressure cell (Aminco) operated at 1000–1250 p.s.i. TRITON X-100™ (t-octylphenoxypolyethoxyethanol) (2% ) is added and the broken cell mixture is stirred for 20 minutes. Particulate matter is removed by centrifugation at 15,000 rpm for 45 minutes in a Sorvall, RC-5Refrigerated Superspeed Centrifuge using an SS34 rotor. The supernatant is withdrawn by syringe from underneath the floating chlorophyll fraction, and approximately 9 ml is layered on each of six buffered sucrose step gradients comprising (from bottom to top) 2M sucrose (4 ml), 1M sucrose (8 ml), 0.5M sucrose (7 ml) and 0.25M sucrose (7 ml), all in 0.75M KPi. Gradients are centrifuged 12–18 hours at 25,000 rpm in an SW27 rotor. Following centrifugation, green, brown, brown-red, purple-red, purple and clear layers (top to bottom) can be discerned with varying resolution. Only the purple-red (reds and phycobiliprotein aggregates) and purple (phycobilisome) bands are retained. Purple-red bands are withdrawn by suction using a pasteur pipet, pooled and stored at 2°–8° C. Stabilized and conjugated rods may be prepared from this fraction, purified by gel chromatography, and immobilized. Purple phycobilisome bands in the 1.0M sucrose layer are withdrawn, pooled, diluted four-fold with KPi buffer and centrifuged at 15,000 rpm for 40 minutes in an SS34 rotor. Resultant supernatants are withdrawn from pelleted sediment (if any) and centrifuged at 30,000 rpm for two hours in a VTi50 rotor. Final supernatants are quickly and carefully aspirated, and phycobilisome-containing pellets are resuspended in a minimal volume of KPi buffer. Protein concentration can be determined by the method of Lowry et al. (1951). Protein measurements are carried out with the Folin phenol reagent *J. Biol. Chem.* 193:265–275 using bovine serum albumin as standard with suitable controls for sucrose and TRITON X-100™ (t-octylphenoxypolyethoxyethanol) interference. Absorption spectra were measured with a Shimadzu Model UV-160 recording spectrophotometer. Fluorescence spectra were recorded at room temperature in a 4 ml quartz cuvette with a SPEX FLUROMAX™ (scanning excitation/emission fluorometer) coupled to a Compudyne PC.

In general, phycobilisome emission spectra can be obtained by exciting phycobilisomes at the absorption maximum of the distal sensitizing phycobiliprotein (e.g., 545 nm for *P. cruentum* B-PE). Phycobilisomes can be routinely characterized by 1) peak absorption per mg protein (e.g., $AU_{545}$ /mg for *P. cruentum*), 2) fluorescence signal per defined concentration (e.g., cps at Emax for intact phycobilisomes at 10 ng/ml), and 3) one or more fluorescence ratios reflecting the efficiency of inter-phycobiliprotein energy transfer (e.g., 666/573 nm emission for *P. cruentum* as an index of APC/B-PE coupling).

LARGE-SCALE ISOLATION OF PHYCOBILISOMES WITHOUT GRADIENT ULTRACENTRIFUGATION

The convenience, scale and cost-effectiveness of phycobilisome isolation by conventional methods (e.g., Gantt and Lipschultz (1972) supra, Gantt et al. (1979) supra) are severely limited by the need for gradient ultracentrifugation. To enable scalable and economical production of phycobilisomes, procedures were developed for isolating phycobilisomes from different organisms without gradient ultracentrifugation. Methods based on those for *Anabaena variabilis* using TRITON X-100™ (t-octylphenoxypolyethoxyethanol) solubilization and PEG precipitation failed to yield intact phycobilisomes from other organisms, notably *P. cruentum*. An additional treatment step is required to protect *P. cruentum* phycobilisomes during removal of TRITON X-100™ (t-octylphenoxypolyethoxyethanol) and PEG. Either sucrose or formaldehyde treatment was found to be effective. Summarized below is the sucrose treatment procedure, which has been validated with modification for both rhodophytes (e.g., *P. cruentum*) and cyanophytes (e.g., *Anabaena variabilis, Spirulina platensis*). Preparative scale can be readily varied by selecting different centrifuge and rotor combinations and adjusting volumes accordingly.

Cells are suspended in 5 ml 0.75M KPi (pH 6.8) per gram wet weight. PMSF and benzamidine are added to a final concentration of 1 mM and 5 mM, respectively, and the suspension is passed through a French pressure cell three times at 1000–1250 p.s.i. Membrane-associated phycobilisomes are solubilized by treatment with 2% TRITON X-100™ (t-octylphenoxypolyethoxyethanol) in 0.75M KPi (pH 6.8) for 20 minutes with stirring. The broken cell preparation is centrifuged at 15,000 rpm for 20 minutes in a Sorvall RC-5B Refrigerated Superspeed Centrifuge using an SS34 rotor to remove membrane fragments and particulate debris. The supernatant is collected by suction from underneath the floating chlorophyll layer. The pellet is discarded. Polyethylene glycol 8000 is added to the supernatant to a concentration of 15% (wt/vol). The mixture is stirred for one hour and centrifuged for 20 minutes at 15,000 rpm in an SS34 rotor. The supernatant is discarded. The pellet is resuspended by addition of 2M sucrose in 0.75M KPi with gentle vortexing to a final concentration of 1.5M sucrose. Thirty minutes following sucrose addition, the suspension is diluted approximately 4-fold with 0.75M KPi (pH 6.8) and centrifuged for three hours at 40,000 rpm (20° C.) in a Beckman L8-M Ultracentrifuge using a VTi50 rotor. The supernatant is discarded. The pellet is resuspended in a minimal volume of 0.75M KPi (pH 6.8), characterized by protein, absorption and fluorescence measurements (cf. supra) and stored either refrigerated or at ambient temperature, depending on the source of phycobilisomes.

STABILIZATION OF PHYCOBILISOMES

In agreement with published studies (e.g., Katoh (1988) Phycobilisome stability. In: Methods in Enzymology Vol. 167, pp. 313–318, Academic Press; and Gantt et al., 1979, supra), isolated phycobilisomes were shown to be unstable to decreases in protein concentration and ionic strength. Intra-phycobilisome energy transfer was disrupted within minutes following dilution of protein (below about 1 mg/ml) or buffer (below about 0.5M KPi), as exhibited by concentration-dependent decreases in the ratio of 666/573 nm fluorescence emission with 545 nm excitation.

To enable reproducible preparation of stable phycobilisome-labeled ligands and receptors for use in conventional specific binding assay configurations, phycobilisomes can first be stabilized. Stabilization methods include, without limitation those discussed below: 1) Covalent stabilization can be accomplished by intra-phycobilisome (inter-subunit) crosslinking, preferably through use of short- or zero-length bifunctional reagents well-known in the art of protein modification (e.g., Wong (1991) *Chemistry of Protein Conjugation and Crosslinking*, CRC Press.). 2) Covalent stabilization can also be achieved by multi-site attachment of natural or synthetic polymers such as carbohydrates, lipids, oligonucleotides, proteins, peptides, polyamino acids, random or ordered copolymers of amino acids, nucleosides, sugars or other small organic molecules. This method for covalent interconnection of phycobilisome subunits can be performed using either one-step or two-step techniques. In the preferred two-step approach, a first reactant (either the phycobilisome or the bridging polymer) is activated in step one. Following removal of excess reagent, the activated reactant is attached in step two to native functional groups on the second reactant. 3) Noncovalent stabilization can be achieved using cosolvents, detergents or other buffer additives that render phycobilisome dissociation thermodynamically unfavorable. 4) Noncovalent, affinity-based stabilization can also be used, using molecules or groups of molecules having a finite affinity for functional binding sites spanning at least two phycobilisome subunits. Molecules having suitable affinity may be selected by either random screening or combinatorial methods from groups consisting of naturally occurring, modified or synthetic antibodies or antibody fragments, oligonucleotides, peptides, proteins, lectins, carbohydrates or polymers of small organic molecules.

Phycobilisomes can be stabilized through a one-step reaction with short to medium chain-length crosslinking agents. Reagents and reaction conditions are selected to favor intra-phycobilisome crosslinking over inter-phycobilisome polymerization. The medium chain-length homobifunctional dialdehyde, glutaraldehyde (GA), and the short chain-length monoaldehyde, formaldehyde (FA), are both effective in protecting phycobilisomes from dilution-induced uncoupling of energy transfer. Maximal stabilization of phycobilisomes with GA is accompanied by partial insolubilization which is only apparent following centrifugation or prolonged storage. GA-induced insolubilization can be minimized through co-optimization of GA and phycobilisome concentrations and reaction time. Alternatively, conditions can be adjusted to yield GA-stabilized phycobilisomes that remain in homogeneous suspension, but sediment completely when centrifuged at 8000 g for two minutes. The stabilizing effect of GA can be improved by sequential treatment of phycobilisomes at low GA/phycobilisome mass ratio (e.g., 0.027% GA/0.727% phycobilisomes) followed by dilution of the reaction mixture with buffered GA to increase the GA/phycobilisome ratio (e.g., to 0.10% GA/0.10% phycobilisomes). In contrast to GA treatment, maximally effective stabilization with shorter chain-length crosslinkers (e.g., FA) can be achieved without loss of soluble phycobilisomes to aggregation or precipitation.

To determine effects of stabilization and conjugation procedures on the size distribution and buoyant density of phycobilisome preparations, the behavior of reaction precursors and products was evaluated on discontinuous sucrose gradients similar to those used for phycobilisome isolation. One-half milligram aliquots of lysine-quenched, GA-stabilized phycobilisomes, unpurified phycobilisome-antibody conjugates and unmodified phycobilisomes were applied to 10 ml sucrose gradients comprising 2.5 ml steps of 2.0M, 1.0M, 0.5M and 0.25M sucrose in 0.75M KPi (pH 7.35). Gradients were centrifuged 20 hours (18° C.) at 50,000 rpm in a 70.1Ti rotor. A purple-red band (rods and B-PE aggregates) appeared in the upper half of the unmodified phycobilisome gradient, indicating some breakdown of native phycobilisomes under these conditions. GA-stabilized phycobilisomes and phycobilisome-antibody conjugate gradients, by contrast, formed a single band in the 1.5M sucrose region. These results suggest that 1) GA treatment successfully prevented phycobilisome dissociation during ultracentrifugation, 2) the one-step GA stabilization/conjugation process did not yield uncontrolled polymerization of phycobilisomes or conjugates, and 3) stabilized phycobilisomes and conjugates remained soluble following covalent crosslinking by methods described herein.

IMMOBILIZATION OF MODIFIED PHYCOBILISOMES TO LATEX MICROSPHERES

FA-treated phycobilisomes and phycobilisome-antibody conjugates ("modified phycobilisomes") quenched with lysine and purified by gel chromatography were immobilized on uniform latex particles either covalently or by passive adsorption. All incubations were performed at room temperature with rotation. Fluorescent and nonfluorescent carboxylate-modified latex microspheres ranging in diameter from 0.03–1 uM were used at final concentrations of 1–10 mg/ml.

Passive adsorption to microspheres was performed for 1–16 hours in 100 mM phosphate (pH 7.2) at immobilization ratios (μg protein/mg particle) ranging from 20–200 ug/mg. Modified phycobilisome-latex suspensions were washed by repeated centrifugation at 8000×g in 100 mM KPi containing 150 mM sodium chloride.

Covalent immobilization was performed at the same protein/particle ratios in a one-step procedure using 1-ethyl-3-(3-dimethylaminopropyl)-carbodiimide EDAC) in 100 mM MES (pH 6.8). Modified phycobilisomes were rapidly spiked into the particle suspension with mixing, allowed to react for 1–2 hours and washed by centrifugation.

For prolonged storage, immobilized phycobilisomes were post-treated with 1% FA in 100 mM KPi (pH 7.4), quenched with lysine, reduced with sodium cyanoborohydride and washed with 100 mM KPi containing 150 mM sodium chloride and 0.05% sodium azide.

IMMOBILIZATION OF ANTIGENS AND ANTIBODIES ON PARAMAGNETIC PARTICLES

Immobilizations were performed at room temperature according to the following protocol.

Amine-modified BioMag™ (Paramagnetic Particles (Advanced Magnetics) was washed five times with vigorous vortexing and magnetic separation in 10 mM sodium phosphate (NaPi; pH 7.35) at a particle concentration of 5–10 mg/ml. After the final wash, the wet cake was resuspended to 25 mg/ml in 6.25% GA (Sigma) and rotated at room temperature for 3 hours. GA-treated particles were washed six times in NaPi. Washed, GA-activated particles were resuspended with PBS (pH 7.2–7.4) containing the protein to be immobilized at 3–10 mg/ml to yield 100–160 ug protein per mg BioMag™ (Paramagnetic Particles). BSA was included as a doping agent to adjust the spacing of immunoreactants on BioMag™ (Paramagnetic Particles) particles. An aliquot of the protein solution was retained for determination of immobilization efficiency. The protein-particle slurry was rotated at room temperature for 16–24 hours. Particles were magnetically separated. The supernatant was decanted and retained for estimation of residual protein. Unreacted GA groups were quenched by resuspension of particles to about 10 mg/ml in 1M glycine (pH 8.0) followed by rotation for one hour. Quenched particles were washed twice in PBS (pH 7.4) and blocked by rotation for two to four hours in PBS containing 2 mg/ml BSA. Blocked particles were washed three times in PBS containing 1 mg/ml BSA, resuspended to a particle concentration of 10 mg/ml and stored at 2°–8° C. Working aliquots were washed three times in assay buffer with thorough vortexing at a particle concentration of about 1 mg/ml prior to use to protect against leaching of immobilized reagents with prolonged storage.

IMMOBILIZATION OF ANTIGENS AND ANTIBODIES TO MICROTITER WELLS

Proteins were passively adsorbed to surface-modified polystyrene microtiter plates by passive adsorption according to the following protocol. Antigens and antibodies were diluted to 2–20 ug/ml in 50 mM carbonate buffer (pH 9.6) or 10 mM sodium phosphate (pH 7.4) in borosilicate glass tubes or 50 ml polypropylene centrifuge tubes immediately before use. Clear polystyrene IMMULON™ (Clear polystyrene 96-well microtiter plates) 4 or white MICROLITE™ (opaque white polystrene 96-well microtiter plates) 4 or white 2 flat-bottomed microtiter plates (Dynatech) were coated at 100 ul per well for 2 hours at 37° C., 4 hours at room temperature (20°–23° C.) or 15–24 hours at 2°–8° C. Plates were decanted and washed once by filling wells with wash buffer (PBS (pH 7.4) containing BSA at 1 mg/ml) and decanting. Wells were blocked for 1 hour with 200 ul PBS containing 2 mg/ml BSA and washed five additional times with wash buffer.

EXAMPLES

Example 1

Specific Binding Assay Using Noncovalent Phycobilisome-Antibody Conjugate

Since unmodified phycobilisomes rapidly dissociate under conditions typically used for preparation and use of specific binding reagents, noncovalent phycobilisome conjugation required careful attention to phycobilisome concentration and reaction conditions at each step of the process. Murine monoclonal anti-phycoerythrin antibody of IgG2b subtype (Sigma Chemical Company) was added dropwise with vortexing to *P. cruentum* phycobilisomes (5.6 mg/ml) in 0.6M KPi (pH 7.2) containing 2.5 mg/ml BSA to yield molar ratios ranging from 0.5–20 IgG2b/phycobilisome. The reaction was allowed to proceed for 30 minutes at room temperature. Immunologic conjugate formation was demonstrated by specific capture of IgG2b-phycobilisome complexes using goat anti-mouse IgG2b antibody immobilized on paramagnetic particles. Fifty microliters of BioMag™ (Paramagnetic Particles)-GAM IgG2b (30 mg/ml washed in 0.75M KPi containing 1% BSA) was added to 40 ul of conjugate mixture containing 200 ug phycobilisomes. After addition of capture reagent, the assay mixture contained phycobilisomes at 2.2 mg/ml with or without bound IgG2b in 0.66M KPi containing 6.7 mg/ml BSA. This mixture was incubated for 30 minutes at room temperature and separated on a magnetic base (Corning). Absorbance at 545 nm was measured using assay supernatants diluted 40-fold in 0.75M KPi. A dose-dependent decrease in absorbance with increasing IgG2b was observed, indicating specific binding of the phycobilisome-IgG2b complex by BioMag™ (Paramagnetic Particles)-GAMIgG2b. Maximal specific binding (26%) occurred at 1–3 ug/test IgG2b, above which binding decreased due to insufficient solid phase capacity.

Example 2

Preparation of a Stable, Modified Phycobilisome Reagent Using Formaldehyde

For most uses of phycobilisomes as detection reagents they must remain structurally intact ("non-dissociated"). For use in heterogeneous specific binding assays (in which bound and free species must be separated intact prior to measurement), phycobilisomes must be stabilized to prevent spontaneous dissociation during conjugation, purification, assay, product manufacturing, shipping and storage. Covalent stabilization methods were developed to preserve the energetic coupling and/or structural integrity of phycobilisomes without compromising solubility. Crosslinkers were used under conditions carefully optimized to avoid precipitation arising from uncontrolled polymerization or charge neutralization. Key optimization parameters included crosslinker type and reactivity, absolute and relative reagent and phycobilisome concentrations, reaction time, pH, and methods for termination and purification. Formaldehyde stabilization, exemplified using *P. cruentum* phycobilisomes, was performed as follows.

Isolated phycobilisomes were adjusted to a protein concentration of 8.0 mg/ml in 0.75M KPi (pH 7.2) containing 0.05% sodium azide. FA (formaldehyde) (11% in 0.75M KPi) was added dropwise with vortexing in a 10% volume to yield a final concentration of 1.0%. The reaction mixture was left standing for 18 hours at room temperature and quenched with 1M L-lysine. For prolonged storage, FA-treated phycobilisomes were reduced with sodium cyanoborohydride and purified over SEPHAROSE™ (beaded agarose) CL-6B equilibrated with 100 mM KPi (pH 7.2) containing 150 mM sodium chloride and 0.05% sodium azide.

Phycobilisome susceptibility to dissociation following dilution was prevented by FA (formaldehyde) treatment in a time- and dose-dependent manner. Preparations treated at varying FA concentrations for 18 hours were incubated for two hours in 0.75M KPi (pH 7.2) at 65 ug/ml and 0.6 ug/ml, respectively, prior to absorption and fluorescence measurements (545 nm excitation).

| [FA] (%) (× 18 hr) | $AU_{545}$ (@ 65 ug/ml) | Fluorescence Emission (@ 0.6 ug/ml) | | Ratio $E_{666}/E_{573}$ |
|---|---|---|---|---|
| | | $E_{666}$ (cps × $10^{-6}$) | $E_{573}$ (cps × $10^{-6}$) | |
| 0 FA control | 0.302 | 1.07 | 1.22 | 0.88 |
| 0.015 | 0.326 | 1.26 | 1.14 | 1.11 |
| 0.05 | 0.359 | 1.38 | 0.63 | 2.19 |
| 0.15 | 0.338 | 1.43 | 0.40 | 3.58 |

-continued

| [FA] (%) (× 18 hr) | AU$_{545}$ (@ 65 ug/ml) | Fluorescence Emission (@ 0.6 ug/ml) | | Ratio E$_{666}$/E$_{573}$ |
| --- | --- | --- | --- | --- |
| | | E$_{666}$ (cps × 10$^{-6}$) | E$_{573}$ (cps × 10$^{-6}$) | |
| 0.50 | 0.368 | 1.45 | 0.38 | 3.82 |
| 1.00 | 0.357 | 1.46 | 0.36 | 4.06 |

Optimal preservation of energy transfer was obtained at 1% FA. Treatment with 2% FA for five hours provided equivalent protection.

Similar FA treatment conditions were required to stabilize phycobilisomes against dissociation in reduced ionic strength buffers. FA-treated phycobilisomes were diluted to approximately 0.75 ug/ml in 0.1M KPi and left standing for 40 hours at room temperature. Fluorescence data for preparations treated with 1% FA for increasing intervals are summarized below:

| treatment time (hrs) | Fluorescence (cps × 10$^{-6}$ @ 0.75 ug/ml) | | Ratio E$_{666}$E$_{573}$ |
| --- | --- | --- | --- |
| | E$_{666}$ | E$_{573}$ | |
| 0 | 0.45 | 6.25 | 0.07 |
| 2 | 1.88 | 1.02 | 1.84 |
| 5 | 2.06 | 1.00 | 2.06 |
| 18 | 2.31 | 0.91 | 2.54 |

To determine whether the stabilizing effect of FA was accompanied by formation of large, insoluble polymers of crosslinked phycobilisomes, FA-induced precipitation was estimated by centrifugation. Phycobilisomes were treated with FA concentrations up to 3.0%. Reactions were left standing at room temperature for 2–18 hours. Recovery of soluble, modified phycobilisomes was estimated by comparing 545 nm absorbance of thoroughly mixed preparations with supernatants obtained after two-minute centrifugation at 8000×g. Relative percent precipitation was determined by subtracting percent recovery of FA-treated preparations from untreated controls. Only prolonged treatments with high FA concentrations yielded significant precipitation.

| [FA] (%) | % recovery at treatment time = | | | relative % precipitation at time = | | |
| --- | --- | --- | --- | --- | --- | --- |
| | 2 hours | 5 hours | 16 hours | 2 hours | 5 hours | 16 hours |
| 0 FA control | 95.7 | 96.0 | 95.4 | 0 | 0 | 0 |
| 0.5% | 93.5 | — | 97.0 | 2.2 | — | 0 |
| 1.0% | 93.7 | 96.6 | 94.6 | 2.0 | 0 | 0.8 |
| 2.0% | — | 92.4 | — | — | 3.6 | — |
| 3.0% | 92.0 | 78.6 | 40.1 | 3.7 | 17.4 | 55.3 |

No precipitation was observed in FA-modified phycobilisomes (2% FA×5 hours) left standing at room temperature for 18 weeks. In addition, no differences in recovery, conjugation efficiency or immunoassay performance were apparent using FA-treated phycobilisomes prepared with and without mixing. These results indicate that FA-treated phycobilisome preparations behaved as homogeneous solutions for purposes of protein modification, purification, immunoassay and prolonged storage.

FA-stabilized phycobilisomes were routinely stored at room temperature. Reference samples were refrigerated (2°–8° C.) for stability comparisons. FA-stabilized phycobilisomes were characterized by absorption and fluorescence measurements using a Shimadzu Model UV-160 recording spectrophotometer and a SPEX FLUOROMAX™ (scanning excitation/emission fluorometer) fluorometer, respectively.

Example 3

Preparation of a Stable, Modified Phycobilisome Reagent Using Glutaraldehyde

Phycobilisomes were adjusted to a concentration of 2–10 mg/ml, preferably about 8.0 mg/ml, with 0.75M KPi (pH 7.3) containing 0.05% sodium azide. GA (glutaraldehyde) (0.2–1.0% in 0.75M KPi) was added dropwise with vortexing in a 10–50% volume over two minutes or, alternatively, in 3–6 incremental additions over elapsed periods up to three hours. Following addition of GA, the reaction mixture was left standing at room temperature for 1–18 hours. In a preferred stabilization protocol designed to precede conjugation by modified one-step GA methods, a reaction mixture comprising 7.27 mg/ml phycobilisomes plus 0.023% GA was incubated at room temperature for 3 hours before addition of a ligand (e.g., antigen) or receptor (e.g., antibody) containing primary amines. Alternatively, the GA stabilization reaction was terminated by addition of excess primary amines (e.g., 100 mM lysine, arginine, glycine, cysteine or glutamic acid). In a preferred protocol for GA stabilization prior to conjugation or immobilization through groups other than free aldehydes, phycobilisomes (7.27 mg/ml) were first stabilized for 1–2 hours with 0.023% GA followed by a 1–4 hour incubation with an additional 5–10 volumes of 0.05–0.15% GA. The reaction was terminated by addition of 100 mM lysine, glycine, cysteine, glutamic acid or an alternative primary amine-containing quench agent. GA-stabilized phycobilisomes were characterized by absorption and fluorescence measurements in accordance with methods used for unmodified phycobilisomes and FA-stabilized phycobilisomes. Stabilized phycobilisomes from *P. cruentum* reproducibly met the following specifications:

Absorptivity: >4 AU$_{545}$/mg (mean about 5.0)

Fluorescence signal (666 nm): >10$^4$ cps at 1 ng/ml with excitation at 545 nm

Fluorescence ratio: 666/573 nm emission ratio >3.0 with excitation at 545 nm

The stabilizing effect of GA was tinted as follows. GA (0.03–3.0% in 0.75M KPi) was added dropwise with mixing to phycobilisomes in 0.75M KPi to yield reaction mixtures comprising 10 mg/ml phycobilisomes and GA at concentrations ranging from 0.003% to 0.3%. After 12 hours at room temperature, reactions were quenched with 100 mM glycine and stored at room temperature for two weeks prior to evaluation.

Stability to dilution was determined by incubating resultant preparations at 10 ug/ml for varying periods of time in 0.75M KPi (pH 7.2). Concentrated phycobilisome stocks were diluted to 10 ug/ml at time zero. Emission spectra of diluted preparations were recorded at varying time intervals with 545 nm excitation. Fluorescence data are expressed as E$_{666}$/E$_{573}$ ratios. Time-zero ratios (30 seconds post-dilution) averaged 2.10 for untreated controls compared to 3.21 for the 0.03% GA-treated phycobilisomes, indicating significant dilution-dependent dissociation of controls within 30 seconds.

| Treatment | Empirical result | Absorption: major peaks | $AU_{545}$ (10 ug/ml) | Post-dilution $E_{666}/_{573}$ ratio | | |
|---|---|---|---|---|---|---|
| | | | | t = 1 hr | t = 18 hr | change |
| 0 GA control | homogeneous purple liquid | 545 > 565 | 0.052 | 1.04 | 0.70 | −33% |
| 0.003% GA | no apparent change | 545 > 565 | 0.049 | 1.31 | 0.98 | −25% |
| 0.01% GA | no apparent change | 545 > 565 | 0.051 | 2.05 | 1.72 | −16% |
| 0.03% GA | slightly hazy, trace settling | 545 > 565 > 350 | 0.055 | 3.04 | 3.01 | −1% |
| 0.10% GA | cloudy with aggregation | 545 > 350 | 0.051 | 3.41 | 3.23 | −5% |
| 0.30% GA | precipitation, discoloration | 550 > 350 | 0.033 | ND | ND | ND |

Stabilization to reduced ionic strength by subprecipitating concentrations of GA was assessed by monitoring fluorescence spectra of control vs. 0.03% GA-treated phycobilisomes following dilution in varying mixtures of deionized water and 0.75M KPi. The stabilizing effect of 0.03% GA treatment was dramatically apparent within one hour of dilution:

| [KPi] (mM) | phycobilisome emission ($E_{666} \times 10^{-7}$ cps) following excitation at 545 nm | |
|---|---|---|
| | Untreated | GA-treated |
| 750 | 1.68 | 1.69 |
| 250 | 1.47 | 1.67 |
| 100 | 1.11 | 1.68 |
| 30 | 0.65 (shoulder) | 1.66 |
| 10 | 0.50 (no peak) | 1.61 |
| 0.75 ($H_2O$ diluent) | 0.46 (no peak) | 1.56 |

Details of the quench, reduction and purification steps of the GA (and FA) stabilization process were varied for different applications. Properties of aldehyde-treated phycobilisomes could be varied by quenching reactions with different amino acids (e.g., glycine, D-arginine, L-lysine). In addition, new chemical groups could be conveniently introduced by selecting suitable quench agents (e.g., L-cysteine for introduction of thiol groups, glucosamine for introduction of sugar groups). For example, phycobilisomes were treated with 0.023% GA, quenched with 10 mM L-cysteine and either stored for subsequent use or reduced, purified and conjugated as follows. Cysteine-quenched, GA-treated phycobilisomes were reduced with 30 mM dithioerythritol and purified over SEPHAROSE™ (beaded agarose) CL-6B equilibrated with 100 mM KPi containing 100 mM NaCl (pH 7.4). Pyridyl-derivatized streptavidin was prepared by established methods using SPDP in 100 mM sodium phosphate (pH 7.4) at an SPDP/streptavidin molar ratio of 10. The product was purified by dialysis in the same buffer and reacted with thiolated phycobilisomes at streptavidin/phycobilisome molar ratios ranging from 2 to 10. The thiolated phycobilisomes were added to the conjugation reaction immediately following reduction. Streptavidin-phycobilisome conjugates were purified over SEPHAROSE™ (beaded agarose) CL-6B. Biotin-specific binding was demonstrated using biotinylated BSA immobilized on paramagnetic particles as the capture reagent.

Example 4

Storage of Phycobilisomes and Modified Phycobilisomes in Dehydrated Form

Dry-reagent formats are preferred for many diagnostic tests and kits as a means of eliminating reagent addition steps, improving reproducibility and increasing shelf-life. Lyophilization (freeze-drying) is a common method of drying reagents for long-term storage. Literature suggests that phycobilisomes are unstable to freezing. (See, e.g., Gantt and Lipschultz (1972) "Phycobilisomes of Porphyridium Cruentum", *J. Cell Biol.*, 54:313-324; Canaani et al. (1980) "Reassembly of Phycobilisomes from Allophycocyanin and a Phycocyanin-Phycoerythrin Complex", *FEBS Letters*, 115 (2):225-229.) Freeze-drying of phycobilisomes and conjugates was undertaken to establish feasibility of dry-reagent phycobilisome product formats.

Phycobilisomes were isolated from *P. cruentum* in 0.75M KPi at 8.8-9.5 mg/ml. Three to twenty microliter aliquots (45-190 µg) were flash-frozen and vacuum evaporated in microtiter wells. The dried phycobilisomes were stored 0-4 weeks at room temperature, resuspended, diluted, and transferred to 3 ml cuvettes for absorbance and fluorescence measurements. Phycobilisomes stored in buffered solution (8.8-9.8 mg/ml in 0.75M KPi containing 0.05% sodium azide) were used as reference.

Absorbance was not affected, while fluorescence was affected slightly. Unmodified phycobilisomes survived freeze-drying and 4-week storage with no change in absorbance. There was a 15-20% decrease in both fluorescence intensity and the 666/573 nm emission ratio with freeze-drying and 4-week storage compared to untreated control. The only significant decrease in fluorescence of freeze-dried preps occurred from time 0 to week 1. No significant changes were noted on storage from week 1 through week 4.

Covalently stabilized phycobilisomes (phycobilisome-antibody conjugates) suffered substantial degradation immediately following freeze-drying in 100 mM KPi containing 150 mM sodium chloride and 0.05% sodium azide. Fluorescence emission at 666 nm decreased by about 60%, 666/573 emission ratios decreased five-fold, and absorption spectra were perturbed. Addition of 1M sucrose prior to lyophilization alleviated all signs of degradation. Conjugate freeze-dried in sucrose-supplemented KPi over 4 weeks showed no significant change in fluorescence or absorbance properties compared to liquid controls or time-zero freeze dried conjugates.

Examples 5

Preparation of Phycobilisome-Antibody conjugate

All steps were performed at room temperature (20°–23° C.). Phycobilisomes isolated from *P. cruentum* were normalized to a concentration of 8 mg/ml in 0.75M KPi (pH 7.35) containing sodium azide (2 mM). GA (0.25%) was added dropwise with vortexing over 2 minutes in a 10% volume to yield a reaction mixture containing phycobilisomes at 7.27 mg/ml and GA at 0.023%. The reaction mixture was left standing for 2 hours. Affinity-purified, Fc-specific goat anti-mouse IgG (GAM; OEM Concepts; 2 mg/ml in 10 mM phosphate-buffered isotonic saline containing 0.1% sodium azide) was added dropwise with vortexing to yield a GAM/phycobilisome molar ratio of 12:1 (128 ug GAM per mg phycobilisomes). After a 4-hour incubation, the reaction was terminated by addition of a 10% volume of 1.1M L-lysine. The quenched reaction was mixed by rotation for one hour. A 5% volume of fleshly prepared sodium borohydride (Aldrich; 5 mg/ml in 0.1 mM NaOH) was spiked into the reaction mixture with vortexing, followed 5 minutes liter by a 10% volume of the same solution. The borohydride-reduced reaction mixture was stored at 2°–8° C. until purification by ultracentrifugation or, preferably, gel chromatography using SEPHACRYL™ (cross-linked co-polymer of allyl dextran and N,N'-methylenebisacrylamide) S300 or SEPHAROSE™ (beaded agarose) CL-6B (Pharmacia) equilibrated in 100 mM KPi (pH 7.35) containing 150 mM NaCl and 0.05% $NaN_3$.

The conjugates were assessed on the basis of: % recovery (yield of soluble phycobilisome conjugate as a percentage of phycobilisome starting material, accounting for procedural losses); absorptivity (AU/mg); fluorescence (concentration-normalized emission intensity; peak ratios); and specific binding in a competitive fluoroimmunoassay using BioMag™ (Paramagnetic Particles)-MIgG as solid phase capture reagent.

Recovery of soluble material estimated for conjugates purified by ultracentrifugation ranged from 72–100%, averaging about 90%. Twelve conjugates prepared from a single lot of phycobilisomes yielded E666/E.573 ratios of 2.92–3.55 (mean=3.16). Normalized fluorescence intensity ($E_{666}$ at fixed input) averaged $4.15 \times 10_6$ cps at a conjugate concentration of 1 ug/ml.

Up to 60% specific binding of conjugates to BioMag™ (Paramagnetic Particles)-MIgG was demonstrated with the solid phase reagent in pseudo-excess (complete saturation was not attempted). Representative binding data are presented below. Fifty microliters of phycobilisome-GAM conjugate (80 ug/ml) was added to test tubes containing 50 ul of buffer with or without MIgG plus 100 ul BioMag™ (Paramagnetic Particles)-MIgG (1 mg/test). Assay tubes were vortexed and incubated for 60 minutes at room temperature. Fluorescence was determined in a volume of 3 ml using 160 ul of assay supernatant withdrawn after magnetic separation.

| MIgG (mass/test) | Supernatant $E_{666}$ (cps × $10^{-5}$) | % bound | MIgG inhibition (cps × $10^{-5}$) |
|---|---|---|---|
| 0 | 22.44 | 42.1 | — |
| 1 ng | 27.91 | 28.0 | 5.47 |
| 10 ug | 38.77 | 0.0 | 16.33 |

GA was also used to conjugate (GAM antibody to FA-stabilized phycobilisomes. Phycobilisomes were treated with 2% FA for four hours, quenched with 1M L-lysine and chromatographed over SEPHAROSE™ (beaded agarose) CL-6B. Stabilized phycobilisomes appearing in the void volume were treated with GA and reacted overnight with antibody at a 12:1 molar ratio. Lysine quench, borohydride reduction and purification were performed as per GA conjugation methods (supra). Resultant conjugates exhibited 666/573 ratios over 3.0 and 60% specific binding to BioMag™ (Paramagnetic Particles)-MIgG. No significant decrease in fluorescence intensity ($E_{666}$) or immunoreactivity (% binding) was detected with overnight room temperature storage at working concentration in 10 mM KPi-based assay buffer or with storage for one week in 100 mM KPi-based assay buffer.

Example 6

Competitive Immunoassay with Photometric Detection

Fifty microliters of sample (assay buffer with or without varying concentrations of mouse immunoglobulin (MIgG)) was added to 12×75 mm glass test tubes arranged in a MAGIC™ (Paramagnetic Particles) separator unit with a side-pull magnetic base (Corning). One hundred microliters of freshly washed BioMag™ (Paramagnetic Particles)-MIgG was added at particle concentrations ranging from 0.3–10 mg/ml. Tubes were vortexed, and 50 ul phycobilisome-GAM conjugate (molar ratio of 1.5–18 GAM/phycobilisome) was added at phycobilisome concentrations ranging from 1–100 ug/ml (5–500 mAU/ml). The reaction mixture was vortexed and incubated for one hour at room temperature. Particles were separated by placing the MAGIC™ (Paramagnetic Particles) rack on its magnetic base for five minutes. One hundred sixty microliter aliquots of assay supernatants were transferred to 12×75 mm glass test tubes and subsequently diluted with 100 mM KPi (pH 7.35) to 1 ml for photometric assays or 3 ml for fluorometric assays.

Data presented below represent a checkerboard co-titration of phycobilisome-GAM conjugate and BioMag™ (Paramagnetic Particles)-MIgG, demonstrating that binding is solid phase limited. Percent binding increased dramatically with incremental increases in particle concentration.

| | | Supernatant Absorbance (mAU/ml) | | | % binding at [BioMag] = | | |
|---|---|---|---|---|---|---|---|
| PB-GAM (ug/test) | MIgG ug/test | BioMag™ (paramagnetic particles) = 30 ug/test | BioMag™ (paramagnetic particles) = 100 ug/test | BioMag™ (paramagnetic particles) = 300 ug/test | 30 ug/test | 100 ug/test | 300 ug/test |
| 40 | 10 | 210 | 212 | 213 | | | |
| 40 | 0 | 210 | 200 | 173 | 0.0 | 4.7 | 18.8 |
| 12 | 10 | 66 | 68 | 66 | | | |
| 12 | 0 | 63 | 54 | 44 | 4.5 | 20.6 | 33.3 |
| 3 | 10 | 12 | 12 | 12 | | | |
| 3 | 0 | 12 | 10 | 4 | 0.0 | 16.7 | 66.7 |

In separate experiments, conjugate binding was dramatically increased by working at 10-fold higher concentrations of conjugate and solid phase. Assay sensitivity was determined to be below 100 ng/ml MIgG.

Example 7

Competitive Immunoassay using Fluorescent Detection

Assays were performed according to the methods of example 6, but reagent concentrations were adapted for fluorescent detection. Data presented below were obtained using 250 ng per test of phycobilisome-GAM conjugate and 250 μg per test of BioMag™ (Paramagnetic Particles)-MIgG. Fluorescence was recorded using 545 nm excitation.

| [MIgG] (ng/test) | $E_{666}$ (cps × $10^{-5}$) | % bound | inhibition (cps × $10^{-5}$) |
|---|---|---|---|
| 0 | 3.74 | 24.3 | — |
| 1 | 4.00 | 19.0 | 0.26 |
| 10 | 4.39 | 11.1 | 0.65 |
| 100 | 4.90 | 0.8 | 1.16 |
| 1,000 | 4.94 | 0.0 | 1.20 |

Example 8

Displacement Assay Using Phycobilisome Conjugate Prebound to Immobilized Antigen Washed BioMag™ (Paramagnetic Particles)-rabbit IgG (BioMag-RIgG) was pretreated with phycobilisome-GAM conjugate (molar ratio of 5/1 GAM/phycobilisome) for two hours at room temperature with mixing. The prebound reagent mixture was washed three times in assay buffer and resuspended to a particle concentration of 400 ug/ml. Five hundred microliter aliquots of prebound reagent were added to 12×75 mm test tubes. The assay was performed by adding 50 ul of sample (buffer with or without MIgG) to the mixture, vortexing, and incubating at room temperature for 60 minutes. After magnetic separation, 500 ul of supernatant was transferred to 2.5 ml 0.1M KPi for fluorescence measurements.

| | Fluorescence (cps × $10^{-5}$) | | % of maximal |
|---|---|---|---|
| [MIgG] (ng/test) | $E_{666}$ | displacement | displacement |
| 0 | 10.53 | — | |
| 1 | 10.72 | 0.19 | 6.1 |
| 10 | 10.85 | 0.32 | 10.4 |
| 100 | 11.62 | 1.09 | 35.3 |

-continued

| | Fluorescence (cps × $10^{-5}$) | | % of maximal |
|---|---|---|---|
| [MIgG] (ng/test) | $E_{666}$ | displacement | displacement |
| 1,000 | 12.46 | 1.93 | 62.5 |
| 10,000 | 13.62 | 3.09 | 100.0 |

A microtiter plate assay in displacement format using the same phycobilisome-GAM conjugate prebound to RIgG-coated wells (20 ug/ml) yielded similar results. The lower displaceable signal is due to the lower solid phase binding capacity of microtiter wells compared to paramagnetic particles.

| | Fluorescence (cps × $10^{-5}$) | | % of maximal |
|---|---|---|---|
| [MIgG] (ng/test) | $E_{666}$ | displacement | displacement |
| 0 | 3.43 | — | |
| 1 | 4.11 | 0.68 | 36.8 |
| 10 | 4.78 | 1.35 | 73.0 |
| 100 | 5.25 | 1.82 | 98.4 |
| 1,000 | 5.28 | 1.85 | 100.0 |

Example 9

Sandwich (Immunometric) Immunoassay

Reverse sandwich assays were performed by preincubating MIgG with phycobilisome-GAM conjugate followed by capture of phycobilisome-GAM-MIgG complexes with BioMag™ (Paramagnetic Particles)-rabbit anti-mouse antibody (BioMag™ (Paramagnetic Particles)-RAM). This protocol maximizes assay sensitivity by allowing the primary (dynamic) immunoreaction to proceed in solution, improving assay kinetics and minimizing steric constraints. Alternatively, phycobilisome-GAM conjugate was used as a labeled second antibody to detect monoclonal antibody binding to immobilized rabbit IgG (RIgG) as follows.

Fifty microliters of buffer or mouse anti-rabbit antibody (MAR) was preincubated with 50 ul phycobilisome-GAM conjugate (20–80 ug/ml) for 30 minutes. Immune complexes were captured by addition of 100 ul of freshly washed BioMag-RIgG at a particle concentration of 10 mg/ml. The reaction was allowed to proceed for 60 minutes prior to magnetic separation. Fluorescence measurements were performed following dilution/transfer of 160 ul assay supernatant to 2.84 ml 0.1M KPi.

| [MAR] | 1 ug/test PBsome-GAM | | 2 ug/test PBsome-GAM | | 4 ug/test PBsome-GAM | |
|---|---|---|---|---|---|---|
| (ng/test) | $E_{666} \times 10^{-6}$ | % bound | $E_{666} \times 10^{-6}$ | % bound | $E_{666} \times 10^{-6}$ | % bound |
| 0 | 1.483 | 0 | 2.400 | 0 | 4.147 | 0 |
| 0.1 | 1.392 | 6.1 | 2.322 | 3.3 | 4.196 | 0 |
| 1.0 | 1.142 | 23.0 | 1.786 | 25.6 | 3.430 | 17.3 |
| 10 | 0.823 | 44.5 | 1.289 | 46.3 | 2.107 | 49.2 |
| 100 | 0.697 | 53.0 | 0.992 | 58.7 | 1.709 | 58.8 |
| 1000 | 0.615 | 58.5 | 0.967 | 59.7 | 1.511 | 63.6 |

Example 10

Microtiter-based Immunoassay with Visual Detection

Competitive Assays: White polystyrene MICROLITE™ (opaque white polystyrene 96-well microtiter plates) 2 microtiter plates (Dynatech) were coated by passive adsorption for 15 hours at 2°–8° C. with 2–20 ug/ml MIgG in 10 mM sodium phosphate (pH 7.35). Supernatants were aspirated. Wells were incubated for 60 minutes at room temperature with 200 ul blocking buffer (10 mM phosphate-buffered isotonic saline (PBS, pH 7.4) containing 100 mM potassium phosphate (pH 7.35), 2 mM sodium azide and 2 mg/ml BSA) and washed six times with 250 ul wash buffer (PBS containing 1 mg/ml BSA). After the final wash, plates were inverted on paper towels and drained by blotting vigorously. Fifty microliters of assay buffer (PBS containing 100 mM potassium phosphate (pH 7.35), 2 mM sodium azide and 1 mg/ml BSA) or MIgG (10–1000 ng/well in assay buffer) was added to each well followed by 50 ul of phycobilisome-GAM at 0.5–10 ug/well. Plates were incubated for one hour with shaking at room temperature, decanted, and inspected before and after washing three times with assay buffer. Phycobilisome-GAM binding to immobilized MIgG could be visually discriminated (both before and after plates were washed) as a purplish-pink coating on the bottom and lower insides of wells under the following conditions:

1. MIgG coating concentration >0.5 ug/well; and
2. phycobilisome-GAM conjugate >1 ug/well; and
3. competing [soluble MIgG] <10 ng/well.

Significant nonspecific binding (bound color at 1 ug/well soluble MIgG) was not visibly apparent in washed plates even at the highest concentrations of phycobilisome-GAM. Visually detectable specific binding (color difference ±1 ug/well MIgG) was most dramatically apparent in wells treated with the highest coating and conjugate concentrations (10–20 ug/ml coating×5–10 ug/well phycobilisome-GAM). Under these conditions, the visual detection limit for MIgG was 10–100 ng/test, corresponding to $10^{-12}$–$10^{-13}$ moles/test (about $10^{-9}$M MIgG).

Sandwich Assays: White polystyrene Microlite™ 2 microtiter plates (Dynatech) were coated for 15 hours at 2°–8° C. with 2–20 ug/ml affinity-purified RAM (H+L) antibody in 10 mM sodium phosphate (pH 7.35). Supernatants were aspirated and wells were incubated with 200 ul blocking buffer (as per competition assays) for one hour at room temperature followed by six washes with 250 ul wash buffer (PBS containing 1 mg/ml BSA). After the last wash, plates were inverted and drained on paper towels with vigorous blotting. One hundred microliters of assay buffer or MIgG (10–1000 ng/well in assay buffer) was added to each well, incubated for one hour at room temperature and aspirated. Wells were washed three times with 250 ul wash buffer. Phycobilisome-GAM conjugate was added at 0.5–10 ug/well in 100 ul assay buffer, incubated for two hours at room temperature with shaking, decanted, and inspected before and after three washes with assay buffer. With and without washing, bound phycobilisome-GAM could be visually discerned in wells exposed to MIgG under the following conditions:

1. RAM coating at >0.2 ug/well; and
2. [MIgG] >10 ng/well; and
3. [phycobilisome-GAM] at 1.5–10 ug/well, depending on RAM and MIgG concentrations.

Prior to washing, visual discrimination of wells exposed to 10 ng/ml MIgG compared to assay buffer was marginal. Washing provided only a minor improvement in resolution. No effort was made to optimize the visual detection limit of immunometric microtiter assays by increasing solid phase binding capacity or conjugate concentration, selecting a higher affinity tracer antibody, modifying the assay protocol or buffer composition, or determining preferred conditions for inspection of the bound phase under UV illumination.

Example 11

Immunochromatographic Dipstick with Visual Detection

Competitive Assay Configuration: MIgG was covalently immobilized to localized zones on aldehyde-treated modified polysulfone membranes as follows. ULTRABIND™ (modified polyethersulfone affinity membrane) US800 unsupported membrane with an effective pore size of 0.8 uM (Gelman Sciences) was cut into 20 cm×6 cm sections. MIgG (2–10 mg/ml in 10 mM phosphate-buffered isotonic saline (PBS), pH 7.2, containing 0.1% sodium azide) was manually spotted by graduated capillary pipet (Drummond Scientific) at 4 ul per linear centimeter along a longitudinal line pencilled midway across each section (3 cm from either edge). After air drying for 30 minutes, membranes were incubated with gentle shaking for one hour at room temperature in 50 ml blocking buffer consisting of 1% BSA in 10 mM PBS (pH 7.4), rinsed twice in 100 ml PBS (pH 7.2) containing 0.1% BSA and air dried for 3 hours. Rinsed, dried membranes were then washed for one hour with shaking in PBS (pH 7.2) containing 0.2% Tween 20 and allowed to dry overnight at room temperature.

Phycobilisome-GAM conjugate was applied to MIgG-modified membranes as follows. Dry, washed membrane sections were cut width-wise into 1×6 cm strips. Ten microliters of phycobilisome-GAM conjugate (2.5 $AU_{545}$/ml) comprising approximately 0.5 mg/ml stabilized P. cruentum phycobilisomes and 10 ug/ml immunologically active GAM in 0.5M KPi (pH 7.35) containing 0.1M sucrose was applied over about 1 square centimeter of each 1×6 cm strip midway between one end and the central transverse line of immobilized MIgG. Conjugate-treated strips were air-dried for 30 minutes before use.

Immunochromatographic MIgG dipsticks were evaluated by contacting the conjugate-treated ends of dried strips to buffer (PBS (pH 7.4) containing 1 mg/mi BSA) or MIgG (1 ug/ml in buffer) and allowing samples to wick up strips by capillary action. When the fluid front had migrated 3.5 cm up the buffer-treated strip (about 10 minutes), a purple-pink band appeared at the immobilized MIgG line (3 cm) and grew progressively more intense as the strip became entirely saturated with buffer (about 20 minutes). No band was apparent in strips exposed to MIgG-containing buffer, indicating that binding of phycobilisome-GAM to immobilized MIgG was substantially inhibited by soluble MIgG.

Inspection of strips in a darkroom under long-wavelength (365 nm) ultraviolet illumination failed to reveal localized phycobilisome-GAM fluorescence in MIgG-treated dipsticks. In buffer-treated dipsticks, phycobilisome-GAM bound to immobilized MIgG was apparent as an intense, fluorescent-red band against a dark blue background. This fluorescent band disappeared after strips were air-dried. When water was applied to the visible band on dry, buffer-treated strips, intense localized red (phycobilisomes) and mobile orange (B-PE) fluorescent phases were observed, suggesting partial dissociation of GA-treated phycobilisomes with drying and re-wetting. Similar results were obtained by fluorometric evaluation of phycobilisome-GAM conjugates before and after freeze-drying. The ratio of 666/573 nm emission with 545 nm excitation decreased markedly with drying and reconstitution, suggesting significant uncoupling of fluorescence energy transfer, unless conjugates were pretreated with sucrose or other protectants. Since isolated B-PE is a more intense fluorophore than APC (the terminal acceptor of *P. cruentum* phycobilisomes), dissociation of phycobilisomes between conjugate binding and detection steps provides a means to amplify the fluorescent signal and increase assay sensitivity.

Sandwich Assay Configuration: Immunometric MIgG dipsticks were prepared by methods substantially equivalent to those for competitive dipsticks, except affinity-purified RAM antibody ((H+L chain)-specific; OEM Concepts) was immobilized to ULTRABIND™ (modified polyethersulfone affinity membrane) US800 membranes in place of MIgG. Ten microliters of RAM (2 mg/ml) per linear centimeter was spotted width-wise across 10×6 cm membrane sections, which were then blocked, rinsed, washed and cut into 1×6 cm strips as per MIgG-immobilized membranes. Ten microliters of phycobilisome-GAM conjugate (5.1 $AU_{545}$ /ml) comprising approximately 1 mg/ml stabilized *P. cruentum* phycobilisomes and 20 ug/ml immunologically active GAM in 0.5M KPi (pH 7.35) containing 0.2M sucrose was applied midway between one end and the immobilized RAM line as per competitive dipsticks, and strips were air-dried before use.

Sandwich MIgG dipsticks were evaluated by contacting the conjugate-treated end to PBS-BSA buffer with or without MIgG (1 ug/ml) and allowing the sample to saturate strips by capillary action (about 20 minutes). A distinct purple-pink band formed at the immobilized RAM line in MIgG-treated dipsticks, but not in buffer-treated controls. These results demonstrate specific binding of a soluble, phycobilisome conjugate in an immunometric assay with a detection limit below $6\times10^{-9}M$.

I claim:

1. A homogeneous preparation of isolated, stabilized phycobilisomes, wherein said phycobilisomes do not settle at 1×g within 24 hours.

2. The preparation of claim 1 wherein said phycobilisomes are soluble, wherein upon centrifugation at 1,000×g for 5 minutes, greater than 55% of said phycobilisomes remain in the supernatant.

3. The preparation of claim 1 wherein said phycobilisomes have been modified by covalent attachment of desired chemical moieties.

4. The preparation of claim 1 wherein said phycobilisomes are attached to a molecular species selected from the group consisting of ligands, receptors, and signal-generating molecules.

5. The preparation of claim 4 wherein said molecular species is attached to one type of constituent phycobilisome protein via a polyvalent receptor.

6. The preparation of claim 1 which is stable in the presence of glycerol.

7. The preparation of claim 1 wherein said phycobilisomes are stable to freezing.

8. The preparation of claim 1 wherein said phycobilisomes are stable to dehydration.

9. A preparation comprising phycobilisome heteroconjugates, wherein said heteroconjugates comprise two covalently attached species, wherein said first species is a phycobilisome and said second species is selected from the group consisting of ligands, receptors, and signal-generating molecules.

10. The preparation of claim 9 wherein said phycobilisome conjugates are stable to freezing.

11. The preparation of claim 9 wherein said phycobilisome conjugates are stable to dehydration.

12. The preparation of claim 9 wherein said molecular species is attached to one type of constituent phycobilisome protein via a polyvalent receptor.

13. A preparation of isolated phycobilisomes which are noncovalently bound to a polyspecific ligand or a polyspecific receptor, wherein said ligand or receptor specifically binds to said phycobilisome.

14. A preparation of isolated, phycobilisomes comprising a terminal acceptor phycobiliprotein which emits at a characteristic wavelength, wherein the phycobilisomes have a major emission peak at the characteristic wavelength of the terminal acceptor phycobiliprotein, wherein said phycobilisomes are immobilized on a solid support.

15. The preparation of claim 14 wherein the phycobilisomes are stabilized.

16. The preparation of claim 14 wherein the phycobilisomes are covalently attached to a molecular species selected from the group consisting of: ligands, receptors, and signal-generating molecules.

17. The preparation of claim 14 wherein the phycobilisomes are immobilized on the solid support in a structurally ordered arrangement.

18. The preparation of claim 14 wherein said molecular species is attached to one type of constituent phycobilisome protein via a polyvalent receptor.

19. In a method for performing a specific binding assay wherein a sample comprising an analyte is contacted with a specific binding partner, and the amount of the analyte present in the sample is determined by means of its ability to specifically bind to the specific binding partner, wherein a component of the assay is detectably labeled, said assay component being selected from the group consisting of: the specific binding partner, reagent molecules having the same chemical identity as the analyte, and reagent molecules having the same binding specificity as the analyte, the improvement comprising: using a signal-generating system comprising phycobilisomes as the detectable label.

20. The method of claim 19 wherein said phycobilisomes are attached to said specific binding partner.

21. The method of claim 19 wherein said phycobilisomes are attached to said reagent molecules having the same chemical identity as the analyte.

22. The method of claim 19 wherein said phycobilisomes are attached to said reagent molecules having the same binding specificity as the analyte.

23. The method of claim 19 wherein said phycobilisomes are attached to a ligand or receptor which specifically binds to said assay component.

24. The method of claim 19 wherein said phycobilisomes are attached to said assay component by a noncovalent means.

25. The method of claim 19 wherein said phycobilisomes are attached to said assay component by means of a covalent bond.

26. The method of claim 19 wherein said phycobilisomes have been stabilized.

27. The method of claim 19 wherein said assay is a homogeneous assay in which binding of said analyte to said specific binding partner is measured without separation of bound from unbound specific binding partner.

28. The method of claim 19 wherein said signal-generating system further comprises a terminal acceptor molecule capable of fluorescence upon transfer of directional energy from said phycobilisomes.

29. The method of claim 19 wherein said phycobilisomes were prepared for use by freezing.

30. The method of claim 19 wherein said phycobilisomes were prepared for use by dehydration.

31. A method for performing a specific binding assay comprising:

contacting a sample comprising an analyte with a specific binding partner;

determining the amount of the analyte present in the sample by means of its ability to specifically bind to the specific binding partner, wherein a component of the assay is detectably labeled with a signal-generating system comprising phycobilisomes, said assay component being selected from the group consisting of: the specific binding partner, reagent molecules having the same chemical identity as the analyte, and reagent molecules having the same binding specificity as the analyte.

32. The method of claim 9 wherein said phycobilisome conjugates are immobilized on a solid support.

* * * * *